United States Patent [19]

Paul et al.

[11] Patent Number: 5,162,328
[45] Date of Patent: Nov. 10, 1992

[54] N-[3-[2-(1H-IMIDAZOL-1-YL)ETHOXY]-PHENYL]-4-(2-THIENYL)-2-PYRIMIDINAMINE AND PHARMACOLOGICALLY ACCEPTABLE SALTS

[75] Inventors: Rolf Paul, River Vale, N.J.; Robert G. Kelly, Suffern; Lawrence W. Torley, Washingtonville, both of N.Y.

[73] Assignee: American Cyanamid Company, Stamford, Conn.

[21] Appl. No.: 816,335

[22] Filed: Dec. 31, 1991

[51] Int. Cl.$^5$ .................. A61K 31/505; C07D 409/14
[52] U.S. Cl. .................................... 514/275; 544/331

[58] Field of Search .................. 544/331; 514/275

[56] References Cited

U.S. PATENT DOCUMENTS 4,788,195 11/1988 Torley .................. 514/252

Primary Examiner—John M. Ford
Attorney, Agent, or Firm—Thomas S. Szatkowski

[57] ABSTRACT

N-[3-[2-(1H-Imidazol-1-yl)ethoxy]phenyl]-4-(2-thienyl)-2-pyrimidinamine and pharmacologicaly acceptable salts, useful as antiasthma agents and treatment of allergic diseases and exhibiting improved bioavailability properties.

20 Claims, 4 Drawing Sheets

N-[3-[2-(1H-IMIDAZOL-1-YL)ETHOXY]PHENYL]-4-(2-THIENYL)-2-PYRIMIDINAMINE AND PHARMACOLOGICALLY ACCEPTABLE SALTS

BACKGROUND OF THE INVENTION

1. Field of the Invention

The invention relates to a new compound N-[3- [2-(1H-imidazol-1-yl)ethoxy]phenyl]-4-(2-thienyl)-2-pyrimidinamine and its pharmacologically acceptable salts which exhibit unexpected advantageous bioavailability properties as evidenced by increased plasma half life and to their use in the treatment of asthma and allergic diseases. 2. Description of the Prior Art The bronchospasm of allergic asthma is a consequence of the release of mediators, such as histamine and slow-reacting substances from mast cells. Certain 4, 5, 6-Substituted-N-(substituted phenyl)-2-pyrimidinamines having antiasthmatic activity are disclosed in U.S. Pat. Nos. 4,788,195 and 4,876,252. While the compounds disclosed and synthesized therein are highly active as antiasthmatic and antiallergic agents in several test systems; it is very difficult to predict from those test systems which compound will exhibit sufficient bioavailability to demonstrate the desired anti-asthmatic and anti-allergic pharmacological effects reproducibly and over sustained periods. As it is generally known and accepted that drug activity is correlated with drug plasma concentrations, the effective treatment of asthma is best achieved by an active compound which exhibits enhanced bioavailability as demonstrated by a prolonged residence in plasma at efficacious concentrations. There is a great need for efficacious compounds to be used in the treatment of asthma and having sufficient bioavailability to produce repeatable and long lasting plasma levels in patients.

SUMMARY OF THE INVENTION

It has now been found that N-[3-[2-1H-imidazol-1-yl)ethoxy]phenyl]-4-(2-thienyl)-2-pyrimidinamine and its pharmacologically acceptable salts exhibit unexpected advantageous bioavailability properties as shown by a sustained plasma concentration and a half-life adequate to give sustained anti-asthma and anti-allergic activity. Unexpected advantageous bioavailability properties of the compounds of the present invention are quite significant because a compound possessing a long half-life in blood plasma at an effective concentration represents an efficacious treatment for asthma and allergies. In contrast, compounds not possessing the requisite bioavailability are much less suitable for treatment.

The new compound N-[3-[2-(1H-imidazol-1-yl)ethoxy]phenyl]-4-(2-thienyl)-2-pyrimidinamine is tested in the Rat Passive Cutaneous Anaphylaxis Assay (PCA) and in the Immunologically Stimulated Human Basophils Assay. When the results from these two assays are compared to corresponding results of two closely related compounds 2-methyl-N$^4$-4-[(4-pyridinyl)-2-pyrimidinyl]-1,4-benzene diamine dihydrochloride and N-[4-[2-(diethylamino)ethoxy]phenyl]-4-(4-pyridinyl)-2-pyrimidinamine dihydrochloride which are reported in U.S. Pat. No. 4,788,195, the results, within experimental error, are equivalent with respect to antiasthma activity. However, these antiasthma assays do not and cannot predict bioavailability properties such as which compound will have sustained plasma concentrations with attending sustained pharmacological activity.

The claimed N-[3-[2-(1H-imidazol-yl)ethoxy]phenyl]-4-(2-thienyl)-2-pyrimidinamine compound demonstrated essentially equivalent high activity to the two closely related compounds of U.S. Pat. No. 4,788,195 in the in vitro basophil histamine release assay and the in vivo Rat PCA test. However, neither in vitro activity nor efficacy in a rodent model can predict appropriate bioavailability or pharmacokinetics. However, by testing these compounds in dogs, it has been unexpectedly found that N-[3-[2-1H-imidazol-1-yl)-ethoxy]phenyl]-4(2-thienyl)-2-pyrimidinamine has an increased plasma half-life and reproducibility when compared to two closely related compounds of U.S. Pat. No. 4,788,195, 2-methyl-N$^4$-[4-(4-pyridinyl)-2-pyrimidinyl]-1,4-benzene-diamine dihydrochloride and N-[4-[2-(diethylamino)ethoxy]phenyl-4-(4-pyridinyl)-2-pyrimidinamine dihydrochloride. It is surprising that the N-[3-2-(1H-imidazol-yl)ethoxy]phenyl]-4-(2-thienyl)-2-pyrimidinamine compound would exhibit such superior bioavailability properties, such as plasma concentration and half-life, over such closely related compounds as 2-methyl-N$^4$-[4-(4-pyridinyl)-2-pyrimidinyl]-1,4-benzenediamine dihydrochloride and N-[4-[2-(diethylamino)ethoxy]phenyl]-4-(4-pyridinyl)-2-pyrimidinamine dihydrochloride.

DETAILED DESCRIPTION OF THE PREFERRED EMBODIMENTS

Figure 1:
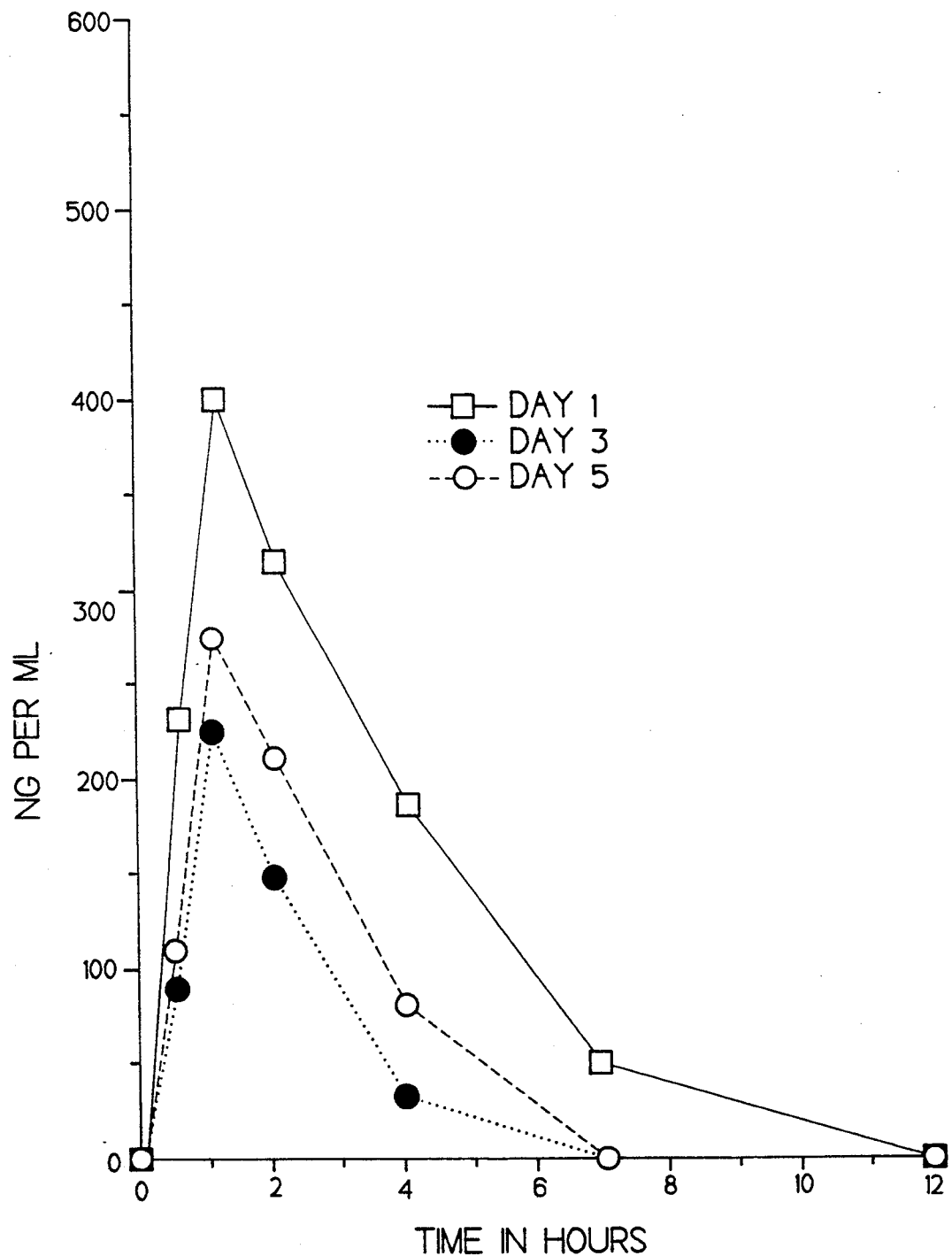
FIG. 1 shows the mean concentration of N-[3-[2-(1H-imidazol-yl)ethoxy]phenyl]-4-(2-thienyl)-2-pyrimidinamine in the plasma of dogs receiving 2 mg/kg/day orally for 5 days.

The novel compounds, N-[3-[2-(1H-imidazol-1yl)ethoxy]phenyl]-4-(2-thienyl)-2-pyrimidinamine 1, and their salts of the present invention may be prepared as set forth in the following reaction scheme.

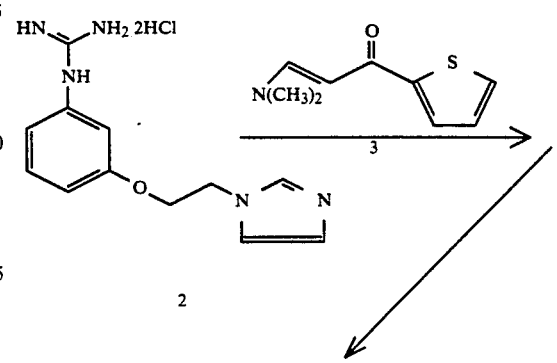

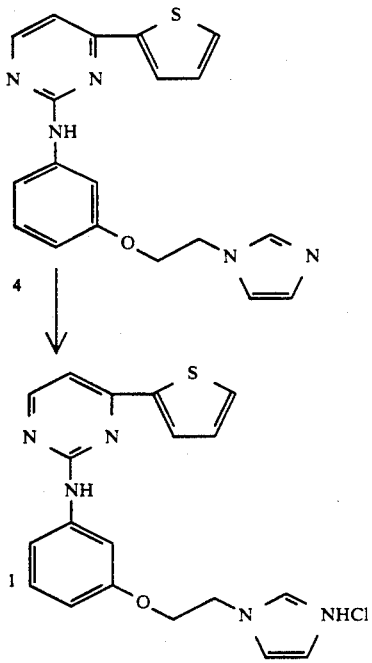

In accordance with the above reaction scheme, [3-[2-(1H-imidazol-1-yl)ethoxy]phenyl]-guanidine dihydrochloride 2 (Example 332, U.S. Pat. No. 4,788,195) is reacted with 3-dimethylamino-1-(2-thienyl)-2-propen-1-one 3 (Example 1, Part A, U.S. Pat. No. 4,374,988) in an inert solvent, N,N-dimethylformamide, and in the presence of potassium carbonate at a temperature of 100° to 155° for 16 to 24 hours to provide, N-[3-[2-(1H-imidazol-1-yl)ethoxy]phenyl]-4-(2-thienyl)2-pyrimidinamine 4. Reaction of 4 with hydrogen chloride affords 1, the monohydrochloride salt.

The organic base of this invention forms non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, maleic, lactic, malic, succinic, tartaric, acetic, fumaric, gluconic, ascorbic, and the like. For purposes of this invention the free base is equivalent to its non-toxic acid-addition salts. The acid-addition salts of the organic free base of the present invention are, in general, crystalline solids.

The novel compound N-[3-[2-(1H-imidazol-1-yl)ethoxy]phenyl]-4-(2-thienyl)-2-pyrimidinamine and pharmacologically acceptable acid-addition salts of the present invention are highly active as an antiasthmatic and antiallergic agent as will be demonstrated hereinbelow.

The bronchospasm of allergic asthma is a consequence of the release of mediators, such as histamine and slow-reacting substances from mast cells. The role of mediator release in the induction of an asthmatic attack has been fully reviewed and documented; see Kaliner, M. and Austen, K. F., Bronchial Asthma Mechanisms and Therapeutics, E. B. Weiss, Editor, Little, Brown and Company, Boston, 163, (1976); Lichtenstein, L. M., Asthma-Physiology, Immunopharmacology and Treatment, Second International Symposium, L. M. Lichtenstein and K. F. Austen, Editors, Academic Press, New York, 51, (1979); and Bell, S. C., et al., Annular Reports in Medicinal Chemistry, 14, 51, H. J. Hess, Editor, Academic Press, New York, (1979). The novel compounds of this invention have been tested by the procedure of Lichtenstein, L. M. and Osler, A. G., J. Exp. Med., 120, 507–530 (1964), which evaluates the ability of compounds to inhibit mediator histamine) release from immunologically stimulated human basophils.

Reagents

10× Concentrated Tris Buffer

Dissolve 140.3 g of sodium chloride, 7.45 g of Trizma-Tris Pre-Set, Reagent Grade, pH 7.6 at 25° C. (Sigma Chemical Co.) in sufficient water to give a final volume of 2 liters.

Human Albumin (Sigma chemical Co.) (30 mg/ml)

Calcium and Magnesium Stocks

Made to 0.075M and 0.5M respectively, with calcium chloride dihydrate and magnesium chloride hexahydrate.

Tris-A Buffer

A 10 ml portion of 10× Tris Buffer and 1.0 ml of human albumin are diluted to 100 ml with water.

Tris ACM Buffer

A 10 ml portion of 10× Tris Buffer, 1.0 ml of human albumin, 0.8 ml of calcium stock and 0.2 ml of magnesium stock are diluted to 100 ml with water.

Rabbit Antihuman IgE

Behring Diagnostics (Generally used at 10 μg protein/ml final concentration).

House Dust Mite Extract (Dermatophagoides Farinae)

Strength 1:100 (w:v) allergenic extract, Hollister-Stier Labs. Generally this is diluted 1:1000 to 1:10,000 (considering the vial as stock).

Other Allergens

Interdermal solutions or intramuscular preparations for hyposensitization, Hollister-Stier Labs. The final concentrations used are on the order of 1 PNU/ml.

Separation of Leukocytes from Human Blood and Subsequent Challenge

Using four 20 ml heparinized tubes, eighty millimeters of blood are withdrawn from subjects with known histamine release to anti-IgE, ragweed antigen or other specific allergen. These 80 ml of blood are mixed with 20 ml of saline containing 0.6 g of dextrose and 1.2 g of dextran. The blood is allowed to sediment at room temperature in two 50 ml polycarbonate centrifuge tubes until a sharp interface develops between the red cells and plasma (60–90 minutes). The plasma, containing the leukocytes, (top) layer from each tube, is withdrawn by pipet and transferred to 50 ml polycarbonate tubes. The plasma is centrifuged for 8 minutes at 110× G at 4° C. The supernatant is carefully poured off as completely as possible and the cell button is resuspended in 2–3 ml of Tris-A buffer using a siliconized Pasteur pipet. The resuspension is accomplished by drawing the liquid gently in an out of the pipet, with the tip below the liquid until an even suspension of cells is obtained. Sufficient Tris-A buffer is then added to bring the volume in the tube to about 45 ml and the tube is centrifuged at 110× G for 8 minutes at 4° C. The supernatant is poured off and the cell button is resuspended and centrifuged as described above. The supernatant is poured off and the cell button is suspended in 2-3 ml of Tris-ACM buffer to make the final volume sufficient to allow addition to the reaction tubes.

Reaction tubes containing anti-IgE or antigens, either alone or with test compound in a total volume of 0.2 ml are prepared and placed in a 37° C. bath. The cells are warmed to 37° C. and frequently swirled to ensure an even suspension, as 1.0 ml aliquots are then added to each reaction tube. The tubes are incubated for 60 minutes at 37° C., vortexing gently every 15 minutes to keep the cells evenly suspended. When the reaction is complete, the tubes are centrifuged at 4° C. for 10 minutes at 1500 rpm to sediment the cells. One ml aliquots of supernatant are transferred to 12 mm by 75 mm polyethylene tubes and 0.2 ml of 8% perchloric acid is added to each tube. Blanks and totals are included in each test. The blanks have cells and all reagents except antigen or anti-IgE. The totals contain 0.24 ml of 8% perchloric acid, one ml of cells and 0.2 ml of buffer. All samples are then centrifuged to remove the precipitated protein.

Assay of Released Histamine by the Automated Fluorometric Method

This automated method has been described by Siraganian, R. P., in Anal. Biochem. 57, 383 (1974) and J. Immunol. Methods, 7, 283 (1975) and is based on the manual method of Shore, P. A., et al., J. Pharmacol. Exp. Ther., 217, 182 (1959).

The automated system consists of the following Technicon Autoanalyzer II components: Sampler IV, Dual-Speed Proportioning Pump III, Fluoronephelometer with a narrow pass primary filter 7-60 and a secondary filter 3-74, Recorder, and Digital Printer. The manifold used is the one described by Siraganian vide supra, with the following modifications: the dialyzer is omitted; all pumping tubes pass through a single proportioning pump with large capacity and twice the volume of sample is taken for analysis.

The automated chemistry consists of the following steps; Extraction from alkaline saline into butanol, back extraction into dilute hydrochloric acid by addition of heptane, reaction of histamine with orthophthaldialdehyde (OPT) at high pH and conversion of the OPT adduct to a stable fluorophore with phosphoric acid. The reaction product is then passed through the fluorometer. The full scale response is adjusted to 50 ng histamine base with a threshold sensitivity of approximately 0.5 ng.

Calculation of the Results of Histamine Release Tests

The instrument blank (wash) is subtracted from the ng histamine of each sample. Then the ng histamine of each sample is divided by the mean of the three totals (cells lysed with perchloric acid) to obtain percent release.

Control samples contain antigen but no test compound. Blank (or spontaneous release) samples contain neither antigen nor test compound. The mean of the blanks (three replicates) is subtracted from the percent release for controls and test compounds.

The means for control and test compound groups are computed and the result for a test compound is computed as percent of control by the formula:

$$100 \times \frac{\% \text{ Histamine Release with Test Compound}}{\% \text{ Histamine Release in Controls}}$$

Values obtained at different concentrations of test compound are used to calculate an $IC_{50}$ (the $\mu M$ concentration which causes a 50% inhibition of histamine release) by linear regression. A compound is considered active if the $IC_{50}$ is $< 48$ $\mu M$.

The results of this test appear in Table 1. These results show the equivalence of these compounds as far as histamine release is concerned. These results do not show bioavailability properties for these compounds.

TABLE I
INHIBITION OF HISTAMINE RELEASE FROM IMMUNOLOGICALLY STIMULATED HUMAN BASOPHILS

| Compound | $IC_{50}$ ($\mu M$) |
| --- | --- |
| N-[3-[2-(1H-Imidazol-1-yl)ethoxy]phenyl]-4-(2-thienyl)-2-pyrimidinamine monohydrochloride | 0.1 ± .01 (n = 3) |
| 2-Methyl-$N^4$-[4-(4-pyridinyl)-2-pyrimidinyl]-1,4-benzenediamine dihydrochloride | 0.9 |
| N-[4-[2-(Diethylamino)ethoxy]phenyl]-4-(4-pyridinyl)-2-pyrimidinamine dihydrochloride. | 0.2 ± .02 (n = 2) |

Rat Passive Cutaneous Anaphylaxis Assay (PCA)

Reagents

Evans' Blue dye: (Sigma Chemical Co.).

Solutions made by dissolving 0.50 g in 100 ml of normal saline.

IgE

Mouse monoclonal IgE (ICN Biochemicals) clone SPE-7 directed against DNP is subdivided into 50 ul aliquots and stored at −70° C.

Allergen

DNP-ovalbumin is made by reacting DNP sulfonic acid with ovalbumin dissolved in saline overnight at room temperature. The resulting solution is dialyzed extensively at 4 C to remove unreacted DNPsulfonic acid and stored as 1 mL aliquots of 100 mg/ml at −70° C.

Animals

Male Wistar strain rats, certified viral free, weighing 250-300 g are obtained from Hilltop Laboratory Animals and housed, in accordance with AALAC standards, on site for at least one week before use.

Sensitization

Forty-eight hours before challenge the rats are shaved on the dorsal surfaces and returned to the cages. Twenty-four hours before challenge the rats are given intradermal injections of 0.1 mL, one on each flank, of saline containing IgE at concentrations ranging from 1000 to 250 ng/mL. These injections give a local dose of 100 to 25 ng IgE. The IgE binds to specific receptors on mast cells in the skin.

Compound administration

Compounds are dissolved, or suspended in distilled water by sonication at concentrations ranging from 0.25 to 0.05 mg/ml immediately before use. The rats are dosed orally by gavage at 10 mL/Kg with the test compound solution or water alone.

Allergen Challenge

To the Evan's blue dye is added sufficient DNP-ovalbumin to make a 1 mg/ml solution. This allergen containing dye is injected intravenously via a tail vein into the rats at 10 ml/Kg. The Evans' blue binds to plasma albumin and remains in the vascular space under conditions of normal capillary permeability. The allergen, which can diffuse into the extravascular space, binds to the IgE on the surface of the cutaneous mast cells and initiates the immediate hypersensitivity response which leads to the release of histamine by intracellular granules of the mast cell. The histamine causes an increase in capillary permeability which allows plasma proteins including the dye tagged albumin to diffuse into the extracellular space resulting in a blue spot in the skin. The size of the lesion is proportional to the amounts of mediators released. This process reaches an optimum in 30 minutes.

Measurement of the response to the allergen

Thirty minutes after challenge the rats are euthanized by $CO_2$. The skin is reflected from the back and the lesion areas estimated as the product of the largest diameter of the bluespot and the diameter perpendicular to it. A compound which is a mediator release inhibitor will reduce the spot area.

Analysis

The effectiveness of the compounds is determined by Analysis of Variance of the lesion areas grouped by IgE dose and compound. Compounds are considered active at the $P<0.05$ level.

Analysis of Results

Table II contains the results of the experiments expressed as the areas of the lesions in $mm^2$. The control lesions for these experiments are also listed. Because more than one compound at a time is tested, some of the control values are repeated in the table. Table III contains the data expressed as a % of the appropriate control. The lesion used in this table is selected as the one corresponding to the dose of IgE that resulted in a control lesion close to 100 $mm^2$ which is found to represent the most sensitive lesion size.

The data shows the equivalence of these compounds as far as histamine release is concerned. These results do not show properties for bioavailability for these compounds.

TABLE II

PASSIVE CUTANEOUS ANAPHYLAXIS LESIONS IN THE RAT ARE INHIBITED BY SINGLE ORAL DOSES OF THE TEST COMPOUNDS

| TEST COMPOUND | DOSE mg/Kg PO 2 HRS | Number of Rats | IgE Dose ng/Site | High IgE Lesion Area | Control Area | IgE | Low IgE Lesion Area | Control Area |
|---|---|---|---|---|---|---|---|---|
| 1 | 2.5 | 5 | 50 | 17 ± 30 | 111 ± 14 (10) | 25 | 8 ± 15 | 63 ± 16 |
|   | 2.0 | 6 | 50 | 103 ± 5 | 248 ± 18 (10) | 25 | 71 ± 20 | 124 ± 25 |
|   |     | 8 | 50 | 119 ± 19 | 275 ± 27 (11) | 25 | 76 ± 14 | 128 ± 30 |
|   | 1.5 | 8 | 50 | 128 ± 43 | 282 ± 49 (8) | 25 | 56 ± 22 | 134 ± 22 |
|   | 1.0 | 7 | 50 | 115 ± 14 | 248 ± 18 (10) | 25 | 71 ± 12 | 124 ± 25 |
|   |     | 5 | 50 | 100 ± 20 | 212 ± 62 (9) | 25 | 8 ± 12 | 128 ± 49 |
|   |     | 9 | 50 | 129 ± 26 | 275 ± 27 (11) | 25 | 78 ± 21 | 128 ± 30 |
|   | 0.5 | 7 | 50 | 216 ± 30 | 248 ± 18 (10) | 25 | 134 ± 21 | 124 ± 25 |
|   |     | 5 | 100 | 320 ± 89 | 317 ± 94 (10) | 25 | 76 ± 55 | 129 ± 43 |
|   |     | 10 | 50 | 87 ± 48 | 226 ± 54 (9) | 25 | 8 ± 17 | 85 ± 87 |
|   |     | 5 | 100 | 108 ± 11 | 216 ± 32 (9) | 25 | 58 ± 53 | 119 ± 20 |
|   |     | 10 | 50 | 106 ± 28 | 312 ± 37 (10) | 25 | 39 ± 41 | 130 ± 9 |
|   |     | 9 | 50 | 136 ± 45 | 275 ± 27 (11) | 25 | 88 ± 17 | 128 ± 30 |
|   | 0.25 | 8 | 50 | 127 ± 19 | 397 ± 35 (10) | 25 | 92 ± 13 | 189 ± 40 |
|   | 0.125 | 10 | 50 | 132 ± 20 | 397 ± 35 (10) | 25 | 87 ± 16 | 189 ± 40 |
| 2 | 1 | 5 | 50 | 123 ± 16[a] | 212 ± 62 (9)[b] | 25 | 10 ± 15 | 129 ± 49 |
|   | 0.5 | 5 | 100 | 217 ± 35 | 215 ± 36 (9) | 25 | 135 ± 20 | 119 ± 20 |
|   |     | 10 | 50 | 157 ± 15 | 312 ± 36 (10) | 25 | 97 ± 7 | 130 ± 9 |
|   |     | 6 | 100 | 362 ± 62 | 299 ± 97 (10) | 25 | 105 ± 12 | 129 ± 43 |
| 3 | 2.5 | 7 | 100 | 105 ± 47 | 235 ± 42 (10) | 25 | 54 ± 38 | 159 ± 24 |
|   | 0.5 | 8 | 50 | 149 ± 22 | 491 ± 78 (8) | 33 | 68 ± 44 | 239 ± 32 |
|   | 0.25 | 8 | 50 | 215 ± 24 | 491 ± 78 (8) | 33 | 108 ± 26 | 239 ± 32 |

[a]Mean ± SD
[b](#) number of controls
1 = N-[3[2-(1H-Imidazol-1-yl)ethoxy]-phenyl]-4-(2-thienyl)-2-pyrimidinamine monohydrochloride.
2 = 2-Methyl-$N^4$-[4-(4-pyridinyl)-2-pyrimidinyl)]-1,4-benzenediamine dihydrochloride.
3 = N-[4-[2-(Diethylamino)ethoxy]phenyl]-4-(pyridinyl)-2-pyrimidinamine dihydrochloride.

TABLE III

SUMMARY OF RAT PCA DATA FOR TEST COMPOUNDS IN TABLE II

| TEST COMPOUND | DOSE PO @ 2 HRS mg/Kg | NUMBER OF RATS | % CONTROL |
|---|---|---|---|
| 1 | 2.5 | 6 | 15.0* |
|   | 2 | 8 | 56.8* |
|   |   | 8 | 43.3* |
|   | 1.5 | 8 | 41.8* |
|   | 1 | 8 | 46.5* |
|   |   | 8 | 47* |
|   |   | 8 | 6.3* |
|   | 0.5 | 5 | 48.5* |
|   |   | 6 | 59.8* |
|   |   | 8 | 87.4 |
|   |   | 10 | 31.8* |
|   |   | 8 | 9.4* |
|   |   | 10 | 30.3* |
|   |   | 8 | 49.5* |
| 2 | 1 | 5 | 57.9* |
|   | 0.5 | 5 | 113.6 |
|   |   | 10 | 74.6 |
|   |   | 6 | 81 |

TABLE III-continued

SUMMARY OF RAT PCA
DATA FOR TEST COMPOUNDS IN TABLE II

| TEST COMPOUND | DOSE PO @ 2 HRS mg/Kg | NUMBER OF RATS | % CONTROL |
|---|---|---|---|
| 3 | 2.5 | 10 | 33.7* |
|   | 0.5 | 10 | 28.6* |
|   | 0.25 | 10 | 45.1* |

*P < 0.05 by ANOVA
1 = N-[3[2-(1H-Imidazol-1-yl)ethoxy]-phenyl]-4-(2-thienyl)-2-pyrimidinamine monohydrochloride.
2 = 2-Methyl-N$^4$-[4-(4-pyridinyl)-2-pyrimidinyl)]-1,4-benzenediamine dihydrochloride.
3 = N-[4-[2-(Diethylamino)ethoxy]phenyl]-4-(pyridinyl)-2-pyrimidinamine dihydrochloride.

Experience and comparisons of the pharmacokinetics and bioavailability of antiasthma compounds in rodents, dogs and man has shown that the dog is a better predictor of the human response than the rat. While not wishing to be bound by theory, it is believed that the prime reason for the superiority of the dog in predicting human response is that the gastrointestinal tract of the dog responds to the agents in a manner similar to man. Therefore the pharmacokinetics of these agents are examined in the dog.

Pharmacokinetics

Since dogs are used in toxicology studies of antiasthma compounds, this species is chosen for pharmacokinetic evaluations. Use of the dog permits the pharmacokinetic comparison of 2 or more compounds in the same test animal, an evaluation which could not be conveniently performed in a smaller species. For each test compound, normal dogs are given a dose of 2.0 mg/kg/day for 5 consecutive days. There is a washout period of 1 month between the study of each of the test compounds in the same four dogs. Each test compound is administered as a solution of 5 mg/ml in either 0.05 or 0.1N HCl which is dispensed into a gelatin capsule immediately prior to dosage.

Heparinized blood samples are obtained from each animal on the first, third and fifth day of dosage at 0.5, 1.0, 2.0, 4.0, 7.0, 12.0 and 24.0 hours after the dose. The samples are centrifuged immediately to obtain plasma which is frozen until analyzed.

Analysis of plasma is performed using High Performance Liquid Chromatography (HPLC). The analytical procedure is essentially identical for each compound. The internal standard used for N-[3-[2-(1H-imidazol-1-yl)ethoxy]phenyl]-4-(2-thienyl)2-pyrimidinamine is 2-chloro-11-(4-methyl-1-piperazinyl)dibenz[b,f][1,4]oxazepine succinate, while for 2-methyl-N$^4$-[4-(4-pyridinyl)-2-pyrimidinyl]-1,4-benzenediamine dihydrochloride and N-[4-[2-(diethylamino)ethoxy]phenyl]-4-(4-pyridinyl)-2-pyrimidnamine dihydrochloride the internal standard is 7-ethoxycoumarin. In a typical procedure, a 0.4 ml volume of acetonitrile containing internal standard is added a 0.2 ml volume of serum. The sample is mixed by vortexing and centrifuged. The clear protein free supernatent fluid is decanted into a clean tube and evaporated to dryness. The dry residue is dissolved in 0.2 ml of HPLC mobile phase and 50 ul of this solution injected. Peaks corresponding to the test compound being measured and to the internal standard compound are quantitated by their absorption of ultraviolet light at 280 nm. Each set of analytical samples is accompanied by the analysis of a group of standard dog plasma samples prepared to contain amounts of the compound being measured which encompasses the concentration range of the samples.

Figure 2:
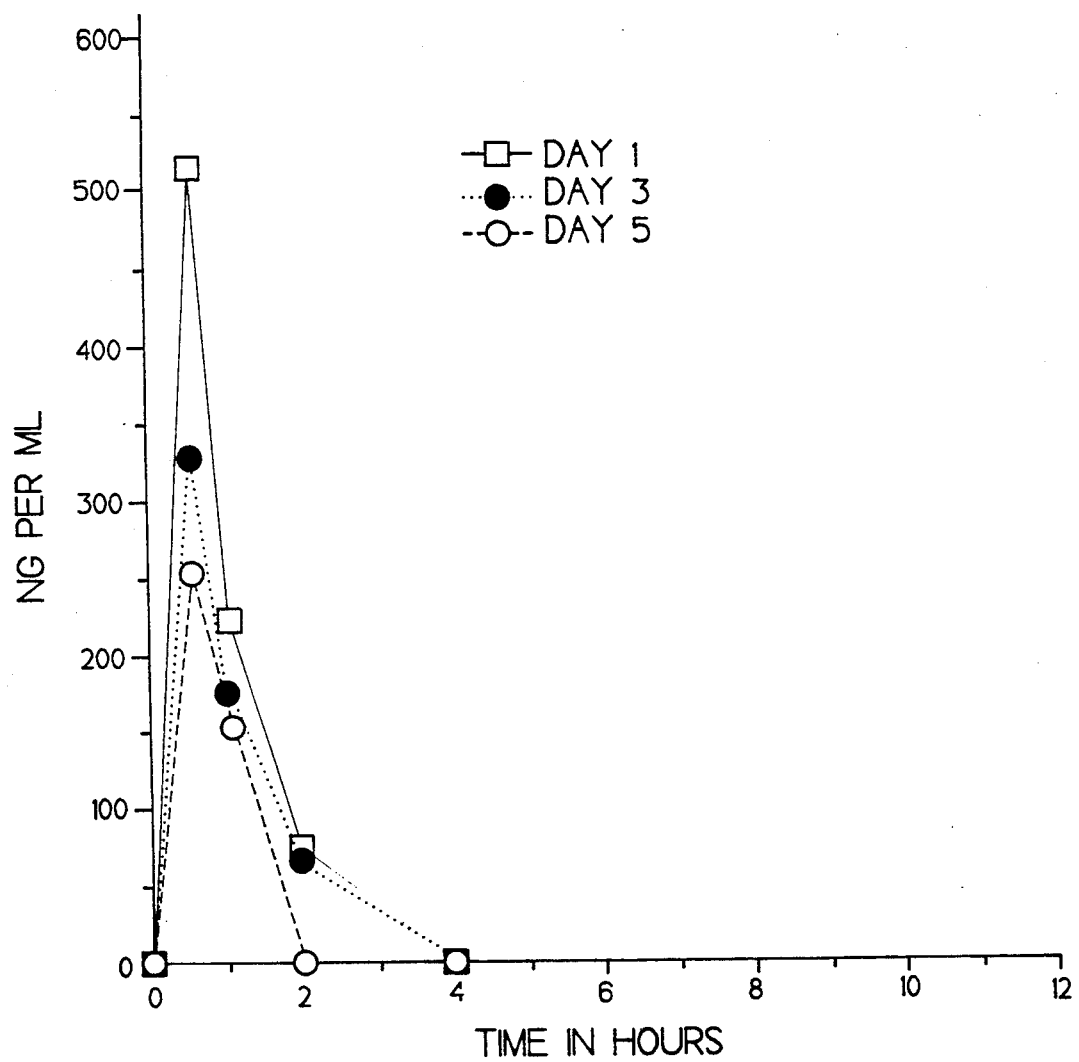
FIG. 2 shows the mean concentration of 2-methyl-N$^4$-[4-(4-pyridinyl)-2-pyrimidinyl]-1,4-benzenediamine dihydrochloride in the plasma of dogs receiving 2 mg/kg/day orally for 5 days.
Figure 3:
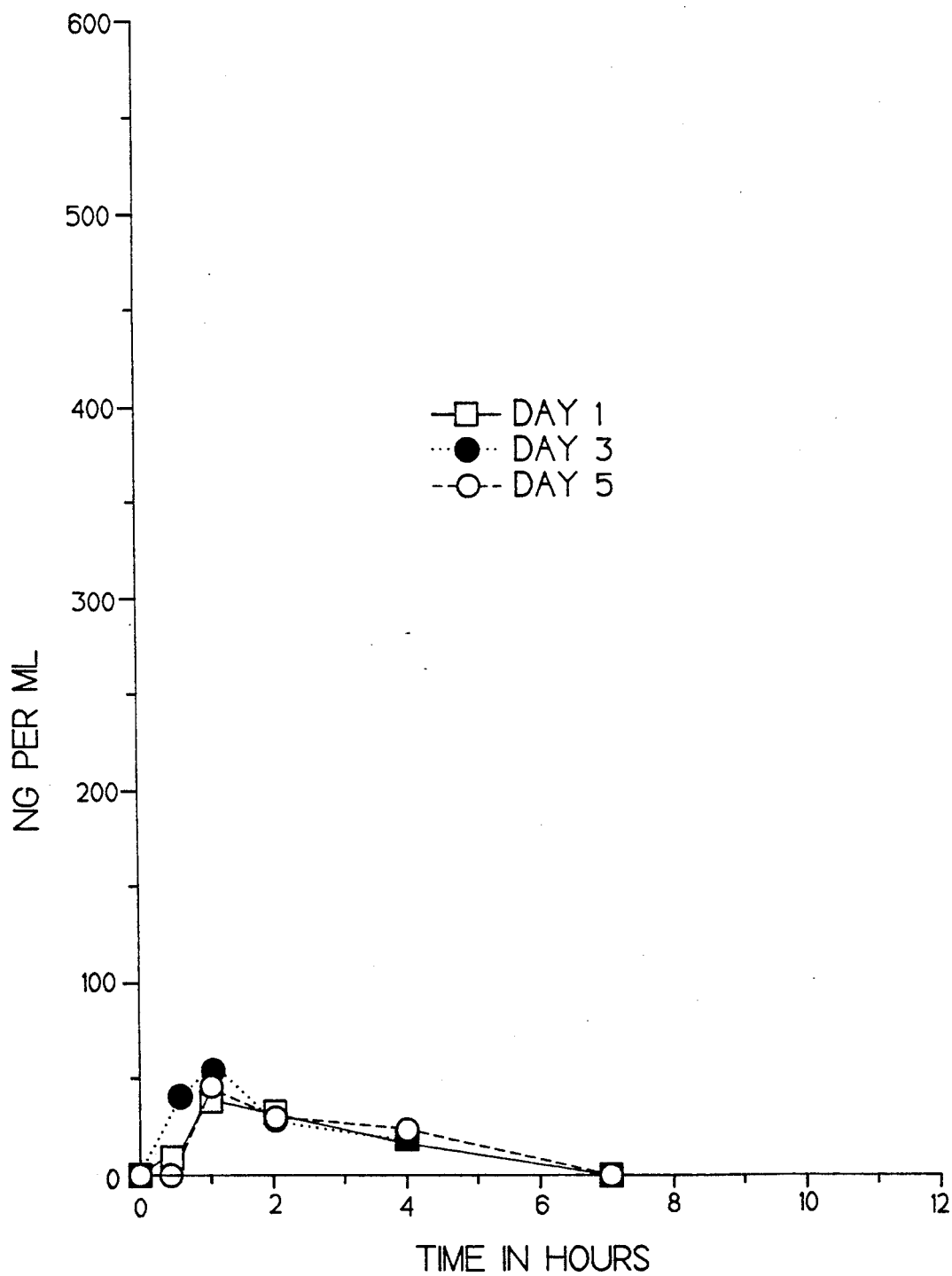
FIG. 3 shows the mean concentration of N-[4-[2-(diethylamino)ethoxy]phenyl]-4-(4-pyridinyl)-2-pyrimidinamine dihydrochloride in the plasma of dogs receiving 2 mg/kg orally for 5 days.
Figure 4:
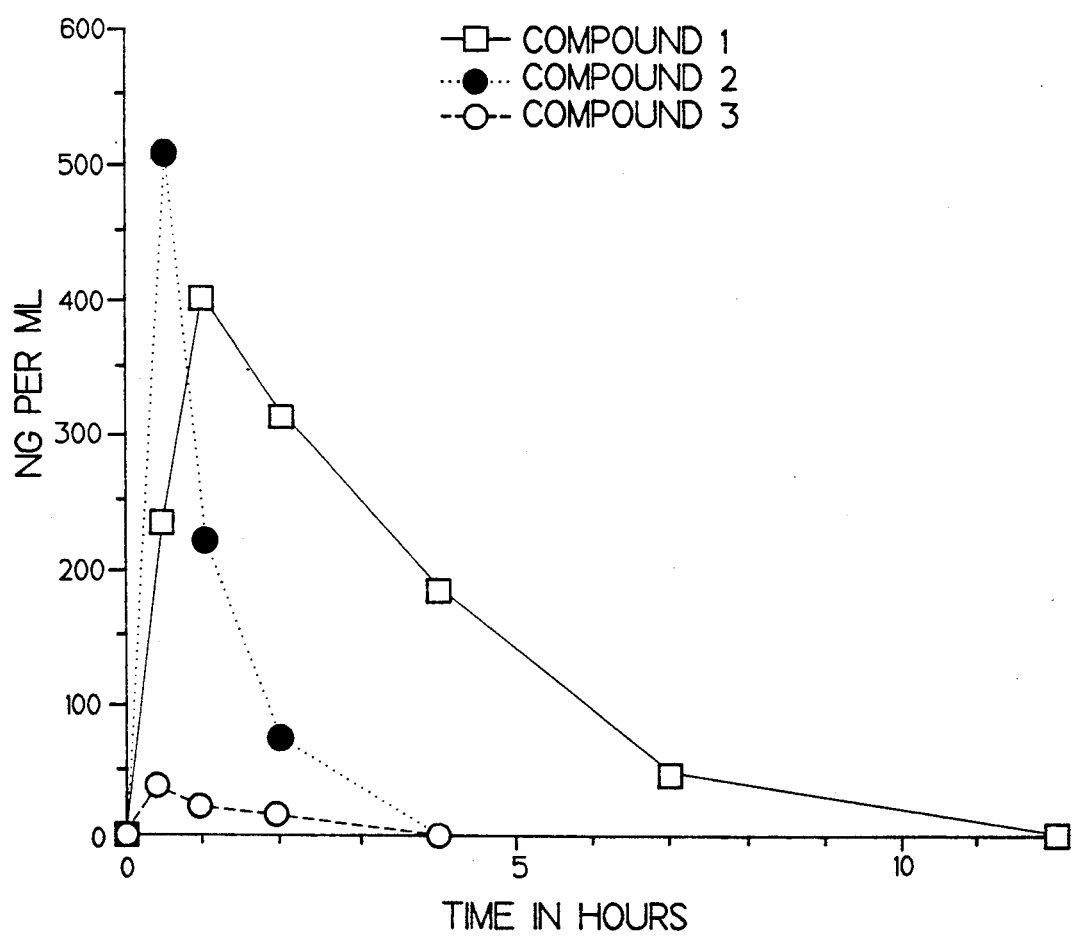
FIG. 4 shows the mean concentrations of test compounds in the plasma of dogs given 2 mg/kg/day orally.

Four normal beagle dogs weighing between 9.2 and 10.2 Kg are used in the study. Analytical results obtained for N-[3-[2-(1H-imidazol-yl)ethoxy]phenyl]-4-(2-thienyl)-2-pyrimidinamine are shown in Table IV. These data are displayed graphically in FIG. 1. Pharmacokinetic parameters derived from these data are shown in Table V. Similar information for 2-methyl-N$^4$-[4-(4-pyridinyl))-2-pyrimidinyl]-1,4-benzene-diamine dihydrochloride are shown in Table VI. These data are displayed graphically in FIG. 2. Pharmacokinetic parameters derived from these data are shown in Table VII. Data for N-[4-[2-(diethylamino)ethoxy]phenyl]-4-(4-pyridinyl)-2-pyrimidinamine di hydrochloride is displayed in Table VIII. Even though four dogs are used in this study only one dog provided measurable concentrations of compound in the plasma. Mean data are displayed graphically in FIG. 3. The data in FIG. 4 displays the plasma levels of the test compounds in the dog after a first dose. The concentration of N-[3-[2-(1H-imidazol-yl)ethoxy]phenyl]-4-(2-thienyl)-2-pyrimidinamine in the plasma over a 12 hour period is shown to be at a higher level for a longer period than the other test compounds.

Since the pharmacological activity of compounds is generally acknowledged to correlate with their concentrations in plasma, it is clear that this compound has exhibited superior bioavailability properties and would be the most efficacious of those tested.

TABLE IV

CONCENTRATION OF
N-[3-[2(1H-imidazol-yl)ethoxy]phenyl]-
4-(2-thienyl)-2-pyrimidinamine
IN THE PLASMA OF DOGS RECEIVING
2 mg/kg/day FOR 5 DAYS
(Concentrations expressed in ng/mL)

| Day | Time in Hours After Dose | Dog 1 | Dog 2 | Dog 3 | Dog 4 | Mean | Std. Dev. |
|---|---|---|---|---|---|---|---|
| 1 | 0.5 | 483 | 185 | 97 | 173 | 235 | ±147 |
|   | 1 | 595 | 334 | 325 | 364 | 405 | ±111 |
|   | 2 | 392 | 251 | 303 | 325 | 318 | ±51 |
|   | 4 | 281 | 161 | 138 | 172 | 188 | ±55 |
|   | 7 | 122 | <30 | 45 | 40 | 52 | ±44 |
|   | 12 | <30 | <30 | <30 | <30 | <30 | ±0 |
| 3 | 0.5 | <30 | <30 | 292 | 65 | 89 | ±120 |
|   | 1 | 125 | 205 | 350 | 220 | 225 | ±81 |
|   | 2 | 98 | 129 | 220 | 144 | 148 | ±45 |
|   | 4 | <30 | 36 | 60 | 38 | 33 | ±22 |
|   | 7 | <30 | <30 | <30 | <30 | <30 | ±0 |
|   | 12 | <30 | <30 | <30 | <30 | <30 | ±0 |
| 5 | 0.5 | 339 | 54 | <30 | <30 | 106 | ±136 |
|   | 1 | 418 | 222 | 272 | 191 | 276 | ±87 |
|   | 2 | 267 | 149 | 233 | 197 | 212 | ±44 |
|   | 4 | 112 | 30 | 114 | 71 | 82 | ±34 |
|   | 7 | <30 | <30 | <30 | <30 | <30 | ±0 |
|   | 12 | <30 | <30 | <30 | <30 | <30 | ±0 |

TABLE V

PHARMACOKINETIC PARAMETERS FOR
N-[3-[2-(1H-imidazol-1-yl)ethoxy]phenyl]-4-(2-thienyl)-2-pyrimidinamine
DOGS RECEIVING 2 mg/kg/day ORALLY FOR 5 DAYS

| Day | | Dog 1 | Dog 2 | Dog 3 | Dog 4 | Mean | Std. Dev. |
|---|---|---|---|---|---|---|---|
| 1 | $C_{max}$ (ng/mL) | 595 | 334 | 325 | 364 | 405 | ±111 |

TABLE V-continued

PHARMACOKINETIC PARAMETERS FOR
N-[3-[2-(1H-imidazol-1-yl)ethoxy]phenyl]-4-(2-thienyl)-2-pyrimidinamine
DOGS RECEIVING 2 mg/kg/day ORALLY FOR 5 DAYS

| Day | | Dog 1 | Dog 2 | Dog 3 | Dog 4 | Mean | Std. Dev. |
|---|---|---|---|---|---|---|---|
| | $T_{max}$ (hr) | 1.0 | 1.0 | 1.0 | 1.0 | 1.0 | ±0 |
| | Half-life (hr)[a] | 2.75 | 2.88 | 1.82 | 1.64 | 2.27 | ±0.55 |
| | $AUC_{O-T}$ (ng hr/mL)[b] | 2161 | 881 | 1159 | 1337 | 1385 | ±477 |
| | $AUC_{O-}$ (ng hr/mL)[c] | 2478 | 1299 | 1276 | 1441 | 1624 | ±487 |
| 3 | Cmax (ng/mL) | 125 | 205 | 350 | 220 | 225 | ±81 |
| | Tmax (hr) | 1.0 | 1.0 | 1.0 | 1.0 | 1.0 | ±0 |
| | Half-life (hr)[a] | — | 1.18 | 1.62 | 1.61 | 1.47 | ±0.21 |
| | $AUC_{O-T}$ (ng hr/mL)[b] | (143) | 383 | 799 | 452 | 444 | ±235 |
| | $AUC_{O-}$ (ng hr/mL)[c] | (398) | 477 | 955 | 551 | 595 | ±215 |
| 5 | Cmax (ng/mL) | 418 | 222 | 272 | 197 | 277 | ±86 |
| | Tmax (hr) | 1.0 | 1.0 | 1.0 | 2.0 | 1.25 | ±0.43 |
| | Half-life (hr)[a] | 1.58 | 0.99 | 1.94 | — | 1.50 | ±0.39 |
| | $AUC_{O-T}$ (ng hr/mL)[b] | 996 | 447 | 682 | (510) | 659 | ±213 |
| | $AUC_{O-}$ (ng hr/mL)[c] | 1287 | 525 | 978 | (694) | 871 | ±290 |

[a]Half-life was estimated for those data sets which provided at least 3 points for an elimination phase
[b]$AUC_{O-T}$ = Area under the plasma concentration-time curve from time of dose to the time of the last measured concentration (T). Values in parentheses were based on fewer than 3 data points.
[c]$AUC_{O-}$ was estimated using an elimination constant of 0.385 per hour, a value derived from the mean of the 10 half-life values which could be calculated from the data above.

TABLE VI

CONCENTRATION OF
2-methyl-$N^4$-[4-(4-pyridinyl)-2-pyrimidinyl]-
1,4-benzenediamine dihydrochloride IN
PLASMA OF DOGS RECEIVING 2 mg/kg/day
ORALLY FOR 5 DAYS
(Concentrations expressed in ng/mL)

| Day | Time in Hours After Dose | Dog 1 | Dog 2 | Dog 3 | Dog 4 | Mean | Std. Dev. |
|---|---|---|---|---|---|---|---|
| 1 | 0.5 | 512 | 438 | 605 | 482 | 509 | ±61 |
| | 1.0 | 233 | 210 | 234 | 206 | 221 | ±13 |
| | 2.0 | 55 | 58 | 184 | <30 | 74 | ±67 |
| | 4.0 | <30 | <30 | <30 | <30 | <30 | ±0 |
| 3 | 0.5 | 375 | 260 | 387 | 283 | 326 | ±56 |
| | 1 | 295 | 78 | 284 | 44 | 175 | ±115 |
| | 2 | 122 | <30 | 141 | <30 | 66 | ±66 |
| | 4 | <30 | <30 | <30 | <30 | <30 | ±0 |
| 5 | 0.5 | 120 | 350 | 105 | 420 | 249 | ±139 |
| | 1 | 277 | 58 | 289 | <30 | 156 | ±129 |
| | 2 | 50 | <30 | <30 | <30 | <30 | ±22 |
| | 4 | <30 | <30 | <30 | <30 | <30 | ±0 |

TABLE VIII

PHARMACOKINETIC PARAMETERS FOR
N-[4-[2-(diethylamino)ethoxy]phenyl]-4-(4-pyridinyl)-
2-pyrimidinamine dihydrochloride
IN PLASMA OF ONE DOG* WHICH RECEIVED
2 mg/kg/day ORALLY FOR 5 DAYS
(Concentrations expressed in μg/mL)

| Time in Hours After Dose | Day 1 | Day 3 | Day 5 |
|---|---|---|---|
| 0.5 | 30 | 124 | <30 |
| 1.0 | 125 | 192 | 153 |
| 2.0 | 102 | 81 | 82 |
| 4.0 | 40 | 34 | 55 |
| 7.0 | <30 | <30 | <30 |
| Cmax (μg/mL) | 125 | 192 | 153 |
| Tmax (hr) | 1.0 | 1.0 | 1.0 |
| Half-life (hr)[a] | 1.77 | 1.25 | 2.16 |
| $AUC_{0-4}$ (ng hr/mL) | 302 | 362 | 293 |

TABLE VII

PHARMACOKINETIC PARAMETERS FOR
2-methyl-$N^4$-[4-(4-pyridinyl)-2-pyrimidinyl]-1,4-benzenediamine dihydrochloride
IN PLASMA OF DOGS RECEIVING 2 mg/kg/day ORALLY FOR 5 DAYS

| Day | | Dog 1 | Dog 2 | Dog 3 | Dog 4 | Mean | Std. Dev. |
|---|---|---|---|---|---|---|---|
| 1 | Cmax (ng/mL) | 512 | 438 | 605 | 482 | 509 | ±61 |
| | Tmax (hr) | 0.5 | 0.5 | 0.5 | 0.5 | 0.5 | ±0 |
| | Half-life (hr)[a] | 0.47 | 0.52 | 0.97 | — | 0.65 | ±0.22 |
| | $AUC_{O-T}$ (ng hr/mL)[b] | 458 | 406 | 570 | (399) | 458 | ±68 |
| | $AUC_{O-}$ (ng hr/mL)[c] | 520 | 471 | 776 | (630) | 599 | ±117 |
| 3 | Cmax (ng/mL) | 375 | 260 | 387 | 283 | 326 | ±56 |
| | Tmax (hr) | 0.5 | 0.5 | 0.5 | 0.5 | 0.5 | ±0.6 |
| | Half-life (hr)[a] | 0.90 | — | 1.02 | — | 0.96 | ±0.6 |
| | $AUC_{O-T}$ (ng hr/mL)[b] | 470 | (293) | 477 | (175) | 354 | ±127 |
| | $AUC_{O-}$ (ng hr/mL)[c] | 602 | (380) | 635 | (224) | 460 | ±168 |
| 5 | Cmax (ng/mL) | 277 | 350 | 289 | 420 | 334 | ±57 |
| | Tmax (hr) | 1.0 | 0.5 | 1.0 | 0.5 | 0.75 | ±0.25 |
| | Half-life (hr)[a] | — | — | — | — | — | — |
| | $AUC_{O-T}$ (ng hr/mL)[b] | (293) | (190) | (125) | (105) | 178 | ±73 |
| | $AUC_{O-}$ (ng hr/mL)[c] | (349) | (255) | (449) | (575) | 407 | ±118 |

[a]Half-life was estimated for those data sets which provided at least 3 points for an elimination phase
[b]$AUC_{O-T}$ = Area under the plasma concentration time from time of dose to the time of the last measured concentration (T). Values in parentheses were based on fewer than 3 data points.
[c]$AUC_{O-}$ was estimated using an elimination constant of 0.893 per hr., a value derived from the mean of the 5 half-life values which could be calculated from the data above

TABLE VIII-continued
PHARMACOKINETIC PARAMETERS FOR
N-[4-[2-(diethylamino)ethoxy]phenyl]-4-(4-pyridinyl)-
2-pyrimidinamine dihydrochloride
IN PLASMA OF ONE DOG* WHICH RECEIVED
2 mg/kg/day ORALLY FOR 5 DAYS
(Concentrations expressed in μg/mL)

| Time in Hours After Dose | Day 1 | Day 3 | Day 5 |
|---|---|---|---|
| $AUC_{0-}$ (ng hr/mL)[b] | 374 | 423 | 392 |

*Four dogs were used for the study. Only the animal reported here (Dog 1) provided measurable concentrations (30 ng/mL or greater) of CL 317,800 in the plasma
[a]Plasma half-life was estimated using the 3 measured concentration values of the elimination portion of the plasma concentration-time curve
[b]Area under the curve from 4 hours to infinite time was estimated using an elimination constant of 0.558 per hour, a value derived from the mean of the 3 half-life values reported.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound. The tablets, troches, pills, capsules and the like may also contain the following: a binder such as gum tragacanth, acacia, corn starch or gelatin; excipients such dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristylgamma-picolinium chloride, benzalkonium chloride, phenethyl alcohol, p-chlorophenyl-alpha-glycerol ether, methyl and propyl parabens, and thimerosal. As a practical matter, it is also convenient to employ anti-oxidants. Suitable anti-oxidants include, for example, sodium bisulfite, sodium metabisulfite, and sodium formaldehyde sulfoxylate. Generally, from about 0.05% to about 0.2% concentrations of anti-oxidant are employed.

These compounds may also be administered by inhalation using conventional Aerosol ® formulations.

The invention will be described in greater detail in conjunction with the following specific examples.

EXAMPLE 1

N-[3-[2-(1H-Imidazol-1-yl)ethoxy]phenyl]-4-(2-thienyl)-2-pyrimidiname

A mixture of 99.95 g of [3-[2-(1H-imidazol-1-yl)ethoxy]phenyl]-guanidine dihydrochloride (U.S. Pat. No. 4,788,195) and 36.24 g of 3-dimethylamino-1-(2-thienyl)-2-propen-1-one (U.S. Pat. No. 4,374,988) in ml of methoxyethanol is stirred and warmed slightly to obtain a complete solution followed by the addition of 41.4 g of potassium carbonate. The reaction mixture is stirred and heated to reflux for 24 hours, filtered and the filtrate evaporated in vacuo to an oily concentrate which is partitioned between chloroform and water. Crystals begin to appear. The aqueous layer is extracted (4×300 ml) with chloroform containing 10 ml of ethanol. The combined organic layers are dried ($Na_2SO_4$) and passed through a pad of hydrous magnesium silicate. The filtrate is evaporated in vacuo to give 61.6 g of a dark oil. The product is crystallized from ethyl alcohol three times, following treatment with activated carbon, to afford 34.31 g of tan solid.

EXAMPLE 2

N-[3-[2-(1H-Imidazol-1-yl)ethoxy]phenyl]-4-(2-thienyl)-2-pyrimidinamine hydrochloride To a solution 1.8394 g of N-[3-[2-(1H-imidazol-1-yl)ethoxy]phenyl]-4-(2-thienyl)-2-pyrimidinamine in 25 ml of hot ethyl alcohol is added ml of 3.58N HCl in ethyl alcohol. The solution turns yellow and begins to boil. The reaction mixture is cooled to 0° C., the crystals collected, washed with 1 ml of ethyl alcohol, followed by ether. The yellow crystals are collected and vacuum dried to afford 1.87 g, mp 233°–237° C.

EXAMPLE 3

N-[3-[2-(1H-Imidazol-1-yl)ethoxy]phenyl]-4-(2-thienyl)-2-pyrimidinamine dihydrochloride To a solution of 1.0 g of N-[3-[2-(1H- imidazol-1-yl)ethoxy]phenyl]-4-(2-thienyl)-2-pyrimidinamine in 10 ml of hot ethyl alcohol is added 5 ml of ethyl alcohol containing 0.3 q of HCl. Crystals begin to form and the reaction mixture is cooled. The solid is collected by filtration, washed with ethyl alcohol and dried, mp 238°–253° C.

EXAMPLE 4

N-[3-[2-(1H-Imidazol-1-yl)ethoxy]phenyl]-4-(2-thienyl)-2-pyrimidinamine sulfate(1:1)

To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.27 g of sulfuric acid. Crystals begin to form and the reaction mixture is cooled. The solid is collected by filtration, washed with ethyl alcohol and dried to afford the desired product.

EXAMPLE 5

N-[3-2-(1H-Imidazol-1-yl)ethoxy]phenyl]-4-(2-thienyl)-2-pyrimidinamine phosphate(1:1)

To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.27 g of phosphoric acid. Crystals begin to form and the reaction mixture is cooled. The solid is collected by filtration, washed with ethyl alcohol and dried to afford the desired product.

EXAMPLE 6

N-3-[2-(1H-Imidazol-1-yl)ethoxy]phenyl]-4-(2-thienyl)-2-pyrimidinamine hydrobromide To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.22 g of hydrogen bromide. Crystals begin to form and the reaction mixture is cooled. The solid is collected by filtration, washed with ethyl alcohol and dried to afford the desired product.

EXAMPLE 7

N-[3-[2-(1H-Imidazol-1-yl)ethoxy]phenyl]-4-(2-thienyl)-2-pyrimidinamine monosulfamate To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.27 of sulfamic acid. Crystals begin to form and the reaction mixture is cooled. The solid is collected by filtration, washed with ethyl alcohol and dried to afford the desired product.

EXAMPLE 8

N-[3-[2-(1H-Imidazol-1-yl)ethoxy]phenyl]-4-(2-thienyl)-2-pyrimidinamine 2-butenedioate (1:1)

To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.32 g of maleic acid. Crystals begin to form and the reaction mixture is cooled. The solid is collected by filtration, washed with ethyl alcohol and dried to afford the desired product.

EXAMPLE 9

N-[3-[2-(1H-Imidazol-1-yl)ethoxy]phenyl]-4-(2-thienyl)-2-pyrimidinamine mono(2-hydroxypropanoate)

To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.25 g of lactic acid. Crystals begin to form and the reaction mixture is cooled. The solid is collected by filtration, washed with ethyl alcohol and dried to afford the desired product.

EXAMPLE 10

N-[3-[2-(1H-Imidazol-1-yl)ethoxy]phenyl]-4-(2-thienyl)-2-pyrimidinamine 2-hydroxybutanedioate (1:1)

To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.37 g of malic acid. Crystals begin to form and the reaction mixture is cooled. The solid is collected by filtration, washed with ethyl alcohol and dried to afford the desired product.

EXAMPLE 11

N-[3-[2-(1H-Imidazol-1-yl)ethoxy]phenyl]-4-(2-thienyl)-2-pyrimidinamine butanedioate (1:1)

To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.32 g of succinic acid. Crystals begin to form and the reaction mixture is cooled. The solid is collected by filtration, washed with ethyl alcohol and dried to afford the desired product.

EXAMPLE 12

N-[3-[2-(1H-Imidazol-1-yl)ethoxy]phenyl]-4-(2-thienyl)-2-pyrimidinamine 2,3-dihydroxybutanedioate (1:1)

To a solution of 1.0 q of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.41 g of tartaric acid. Crystals begin to form and the reaction mixture is cooled. The solid is collected by filtration, washed with ethyl alcohol and dried to afford the desired product.

EXAMPLE 13

N-[3-[2-(1H-Imidazol-1-yl)ethoxy]phenyl]-4-(2-thienyl)-2-pyrimidinamine monoacetate To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.17 g of acetic acid. Crystals begin to form and the reaction mixture is cooled. The solid is collected by filtration, washed with ethyl alcohol and dried to afford the desired product.

EXAMPLE 14

N-[3-[2-(1H-Imidazol-1-yl)ethoxy]phenyl]-4-(2-thienyl)-2-pyrimidinamine monogluconate To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.54 g of gluconic acid. Crystals begin to form and the reaction mixture is cooled. The solid is collected by filtration, washed with ethyl alcohol and dried to afford the desired product.

EXAMPLE 15

N-[3-[2-(1H-Imidazol-1-yl)ethoxy]phenyl]-4-(2-thienyl-2-pyrimidinamine compound with L-ascorbic acid(1:1)

To a solution of 1.0 g of N-[3-[2-(1H-imidazol-1-yl)ethoxy]phenyl]-4-(2-thienyl)-2-pyrimidinamine in 10 ml of hot ethyl alcohol is added 5 ml of ethyl alcohol containing 0.48 g of ascorbic acid. Crystals begin to form and the reaction mixture is cooled. The solid is collected by filtration, washed with ethyl alcohol and dried to afford the desired product.

We claim:

1. A compound N-[3-[2-(1H-imidazol-1-yl)ethoxy]phenyl]-4-(2-thienyl)-2-pyrimidinamine and pharmacologically acceptable salts thereof.

2. The compound according to claim 1, wherein the acceptable salts are selected from the sulfate, phosphate, hydrochloride, hydrobromide, sulfamate, maleate, lactate, malic, succinate, tartarate, acetate, fumarate, gluconate, and ascorbate.

3. The compound according to claim 1 (N-[3-[2-(1H-imidazol-1-yl)ethoxy]phenyl]-4-(2-thienyl)-2-pyrimidinamine monohydrochloride salt.

4. The compound according to claim 1 N-[3-[2-(1H-imidazol-1-yl)ethoxy]phenyl]-4-(2-thienyl)-2-pyrimidinamine dihydrochloride salt.

5. The compound according to claim 1 (N-[3-[2-(1H-imidazol-1-yl)ethoxy]phenyl]-4-(2-thienyl)-2-pyrimidinamine sulfate (1:1).

6. The compound according to claim 1 (N-[3-[2-(1H-imidazol-1-yl)ethoxy]phenyl]-4-(2-thienyl)-2-pyrimidinamine phosphate (1:1).

7. The compound according to claim 1 (N-[3-[2-(1H-imidazol-1-yl)ethoxy]phenyl]-4-(2-thienyl)-2-pyrimidinamine hydrobromide.

8. The compound according to claim 1 (N-[3-[2-(1H-imidazol-1-yl)ethoxy]phenyl]-4-(2-thienyl)-2-pyrimidinamine monosulfamate.

9. The compound according to claim 1 (N-[3-[2-(1H-imidazol-1-yl)ethoxy]phenyl]-4-(2-thienyl)-2-pyrimidinamine 2-butenedioate (1:1).

10. The compound according to claim 1 (N-[3-[2-(1H-imidazol-1-yl)ethoxy]phenyl]-4-(2-thienyl)-2-pyrimidinamine mono(2-hydroxypropanoate).

11. The compound according to claim 1 (N-[3-[2-(1H-imidazol-1-yl)ethoxy]phenyl]-4-(2-thienyl)-2-pyrimidinamine 2-hydroxybutanedioate (1:1).

12. The compound according to claim 1 (N-[3-[2-(1H-imidazol-1-yl)ethoxy]phenyl]-4-(2-thienyl)-2-pyrimidinamine butanedioate (1:1).

13. The compound according to claim 1 (N-[3-[2-(1H-imidazol-1-yl)ethoxy]phenyl]-4-(2-thienyl)-2-pyrimidinamine 2,3-dihydroxybutanedioate (1:1).

14. The compound according to claim 1 (N-[3-[2-(1H-imidazol-1-yl)ethoxy]phenyl]-4-(2-thienyl)-2-pyrimidinamine monoacetate.

15. The compound according to claim 1 (N-[3-[2-(1H-imidazol-1-yl)ethoxy]phenyl]-4-(2-thienyl)-2-pyrimidinamine monoglucomate.

16. The compound according to claim 1 (N-[3-[2-(1H-imidazol-1-yl)ethoxy]phenyl]-4-(2-thienyl)-2-pyrimidinamine compared with L-ascorbic acid (1:1).

17. The compound according to claim 1 N-[3-2-(1H-imidazol-1-yl)-ethoxy]phenyl]-4-(2-thienyl)-2-pyrimidinamine.

18. A method of treating asthma and allergic diseases in a mammal which comprises administering to said mammal an effective antiasthma and antiallergic amount of the compound according to claim 1.

19. A method of treating asthma and allergic diseases in a mammal by providing a sustained plasma level of an antiasthma and antiallergic compound which comprises administering to said mammal an effective amount of a compound of claim 1.

20. A method of providing a sustained plasma level of an antiasthma and antiallergic compound in a mammal which comprises administering to said mammal an effective amount of a compound of claim 1.

* * * * *